(12) United States Patent
Hancu et al.

(10) Patent No.: US 7,741,844 B2
(45) Date of Patent: Jun. 22, 2010

(54) METHOD AND SYSTEM FOR MAGNETIC RESONANCE IMAGING USING LABELED CONTRAST AGENTS

(75) Inventors: Ileana Hancu, Clifton Park, NY (US); Richard Philip Mallozzi, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 204 days.

(21) Appl. No.: 11/745,043

(22) Filed: May 7, 2007

(65) Prior Publication Data

US 2008/0278163 A1 Nov. 13, 2008

(51) Int. Cl.
G01V 3/00 (2006.01)
A61B 5/05 (2006.01)

(52) U.S. Cl. .............. 324/308; 324/307; 324/309; 324/317; 324/318; 600/420; 600/421; 600/431; 600/410; 600/411

(58) Field of Classification Search ......... 324/300–322; 600/407–435
See application file for complete search history.

(56) References Cited

U.S. PATENT DOCUMENTS

| | | | | |
|---|---|---|---|---|
| 5,203,332 A | * | 4/1993 | Leunbach | 600/410 |
| 5,263,482 A | * | 11/1993 | Leunbach | 600/412 |
| 5,415,163 A | * | 5/1995 | Harms et al. | 600/420 |
| 6,845,262 B2 | * | 1/2005 | Albert et al. | 600/420 |
| 2004/0119471 A1 | * | 6/2004 | Blanz et al. | 324/303 |
| 2005/0030026 A1 | * | 2/2005 | Pines et al. | 324/309 |
| 2007/0229072 A1 | * | 10/2007 | Appelt et al. | 324/316 |
| 2007/0238954 A1 | * | 10/2007 | White et al. | 600/407 |
| 2008/0278163 A1 | * | 11/2008 | Hancu et al. | 324/309 |

OTHER PUBLICATIONS

Peter M. Joseph and Dongfeng Lu, "A Technique for Double Resonant Operation of Birdcage Imaging Coils", IEEE Transactions On Medical Imaging, Sep. 1989, pp. 286-294, vol. 8, No. 3.

* cited by examiner

*Primary Examiner*—Brij B. Shrivastav
*Assistant Examiner*—Tiffany A Fetzner
(74) *Attorney, Agent, or Firm*—Patrick K. Patnode

(57) ABSTRACT

A method and system for imaging using labeled contrast agents and a magnetic resonance imaging (MRI) scanner are provided. The method comprises performing a prescan at a frequency selected to be substantially similar to a frequency of the labeled contrast agent and performing an examination scan at the frequency of the labeled contrast agent substantially immediately after administering the labeled contrast agent to a subject.

20 Claims, 5 Drawing Sheets

METHOD AND SYSTEM FOR MAGNETIC RESONANCE IMAGING USING LABELED CONTRAST AGENTS

BACKGROUND

The invention relates generally to magnetic resonance imaging (MRI) and analytical magnetic resonance spectroscopy (MRS), more particularly to calibration of MRI and MRS scanners when employing labeled contrast agents such as $^{13}C$ based contrast agents.

Magnetic Resonance Imaging (MRI) and Magnetic Resonance Spectroscopy (MRS) are diagnostic techniques that are particularly attractive to physicians in that the techniques do not involve exposing a patient under study to potentially harmful radiation, such as X-rays. Further, both techniques have advantages over other available imaging platforms when analyzing metabolic characteristics and regions of interest in a patient. Analytical high resolution nuclear MRS is routinely used in the determination of molecular structure.

Until recently, MRI and MRS have lacked sensitivity due to the normally very low polarization of the nuclear spins of the samples used. A number of techniques exist to improve the polarization of nuclear spins in the solid phase. These techniques are known as hyperpolarization techniques and lead to an increase in sensitivity. As used herein, the term "hyperpolarize" or "hyperpolarization" refers to changing the distribution of spins on the available spin states from the Boltzmann distribution. The resulting hyperpolarization is higher than the polarization given by the Boltzmann distribution, which is a function of temperature and magnetic field strength. These concepts and methods for hyperpolarization are further described in U.S. Pat. No. 6,466,814.

In hyperpolarization techniques, a sample of a labeled imaging agent, for example $^{13}C$ Pyruvate or another similar polarized metabolic imaging agent, is introduced or injected into the subject being imaged.

Given the ubiquitous presence of carbon atoms in most metabolic processes, and the large chemical shift of the $^{13}C$ nuclei, $^{13}C$ spectroscopy is very promising for following metabolism in vivo. Given the low gyromagnetic ratio of the $^{13}C$ nuclei, however, even images/spectra aided by the infusion of labeled compounds suffer from low resolution or low signal to noise, making their utility in a clinical setting somewhat questionable.

The recent development of hyperpolarization techniques can dramatically change the impact that $^{13}C$ MRI and MRS can have in managing a variety of pathological conditions. Real time imaging of metabolism has been reported in a variety of animal models of disease using MRI of $^{13}C$ labeled, hyperpolarized compounds. In order to successfully translate the results of research performed in animals to humans, care must be taken when imaging such compounds, to insure that the maximum information is extracted using the minimum relevant agent dose. The hyperpolarized signals are large, non-renewable and fast decaying, and require special attention when imaged, to extract the maximum image signal to noise (SNR) per injected agent dose.

Many pulse sequences require precise flip angle calibration to produce high SNR, artifact-free images. Moreover, quantification of compound concentration relies on precise knowledge of the excitation flip angle. For most MRI or MRS scans, flip angle calibration is performed in a prescan step, at the same frequency as the one used for imaging. For infusion or injection of $^{13}C$ labeled (or labeled and hyperpolarized) compounds, such calibration step is challenged by the low availability of natural abundance signal prior to injection (at least in certain anatomical areas, such as the brain), and by the variable nature of the signal following injection. One approach to overcome these difficulties is to use a phantom loading the coil in a manner similar to the way a patient would load it, and perform a flip angle calibration on that phantom prior to any patient scan. The same transmit gain setting would then be used for all the in vivo studies.

However, in $^{23}Na$ scans of human brains, for example, the transmit power can vary by as much as 2 dB from subject to subject. It is clear, therefore, that a common calibration to be used for all subjects would be imprecise, and could lead to image signal loss for pulse sequences that are sensitive to flip angle calibration (such as spin echoes), or to error in quantifying metabolite concentrations.

What is needed is a system and method and system for imaging using labeled contrast agents, such as metabolic imaging agents, that overcome the problems and challenges described above.

BRIEF DESCRIPTION

In a first aspect, a method for imaging using labeled contrast agents in MRI is provided. The method comprises the steps of: performing a prescan at a frequency selected to be substantially similar to a frequency of the labeled contrast agent and performing an examination scan at the frequency of the labeled contrast agent substantially immediately after administering the labeled contrast agent to a subject.).

In a second aspect, a method for imaging using labeled contrast agents in MRI is provided. The method comprises the steps of: performing a prescan at a frequency different than but substantially similar to a frequency of a labeled contrast agent to calibrate the MRI scanner for a given subject and performing an examination scan substantially immediately after administering a labeled contrast agent to the subject, wherein the examination scan is performed at a frequency corresponding to the labeled contrast agent.

In a third aspect, a system for imaging using labeled contrast agents in MRI is provided. The system comprises: a radiofrequency coil tunable at frequencies corresponding to resonating frequencies of a selected labeled contrast agent and $^{23}Na$ and wherein the MRI scanner is configured to perform a prescan at a $^{23}Na$ frequency to calibrate the MRI scanner. The MRI scanner is further configured to perform an examination scan at the labeled contrast agent frequency substantially immediately after administering a labeled contrast agent to a subject.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
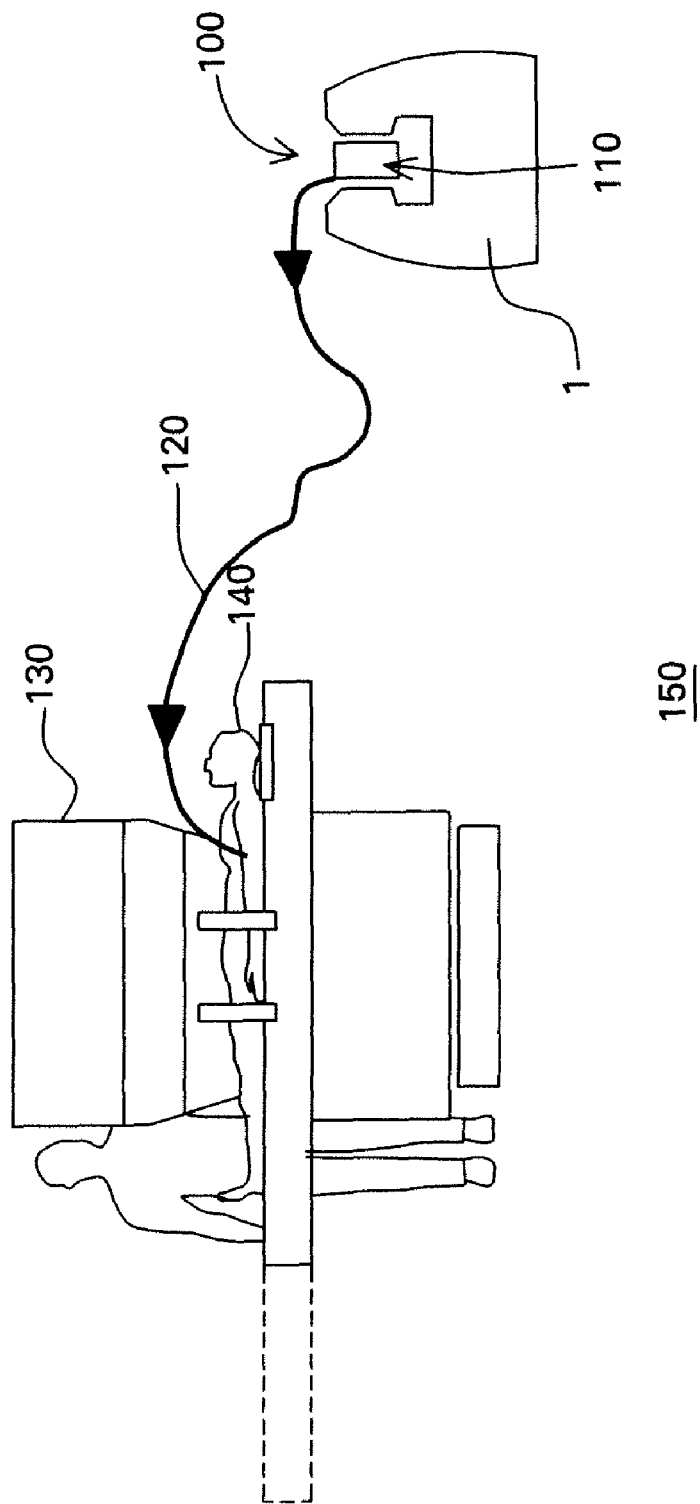
FIG. 1 is an illustration of an exemplary MRI system and polarizing subsystem to which embodiments of the present invention are applicable.

Referring to FIG. 1, a exemplary system 150 is shown for producing hyperpolarized samples for use in a MRI device and includes a cryostat 1 and polarizing subsystem 100 for processing material from container 110 and resulting in the hyperpolarized material. A material delivery line 120 is used to deliver the hyperpolarized material to subject 140 within MRI scanner 130. Delivery to subject may include injection, but other methods of administering the agent to the subject may be envisaged. In the embodiment shown in FIG. 1, the hyperpolarized samples are used in an in vivo imaging application. It is to be appreciated that hyperpolarized samples for Nuclear Magnetic Resonance (NMR) analysis may also be produced using similar methods and techniques as described below.

In methods and devices as shown in FIG. 1, a solid sample of the material to be polarized can be polarized while still in the solid phase by any appropriate known method, e.g. brute force polarization, labeled nuclear polarization or the spin refrigerator method, while being maintained at a low temperature (e.g. under 100 K) in a strong magnetic field (e.g. 1-25 T). After the solid sample has been polarized, it is melted with a minimum loss of polarization. In the following the expression "melting means" will be considered to mean the following: a device capable of providing sufficient energy to the solid polarized sample to melt it or otherwise bring the polarized sample into solution for introduction into the subject being imaged. As used herein, the term "solid" refers to solid materials, semi-solid materials or any combination thereof provided the material requires some transformation to attain a liquid state suitable for introduction into a subject being imaged.

For most solid samples, the relaxation rate (loss of polarization if hyperpolarized) increases rapidly as a function of inverse field strength. Therefore, for these polarized samples it is preferable that they are kept in a strong magnetic field (e.g. greater than 0.1 T) while being handled. Other reasons for the loss of polarization are also known, e.g. sudden changes of magnetic field orientation, strong magnetic gradients, or radio frequency fields, and these should be avoided as much as possible. The melting of the polarized sample can be promoted by several methods, e.g. ultra sound, microwave heating, laser irradiation, radiation or conduction or any other means that will deposit into the solid sample the energy required to melt it. The relaxation rate as a function of temperature and field is unique to every solid sample and solvent/solute system. It is therefore advantageous to optimize the temperature of the process for minimal relaxation of the actual sample being melted. In general, but not always, the magnetic field should be as strong as possible. The minimum $T_1$ during the process will generally increase with increasing magnetic field.

In embodiments of the present invention, the hyperpolarized sample for injection is prepared as described above prior to an in vivo imaging acquisition. It is to be appreciated that the time between preparation of the sample and the imaging is desirably minimized or more desirably the sample is prepared substantially immediately prior to injection so to avoid any decay or loss of polarization or other important signal characteristics of the sample or agent.

Figure 2:
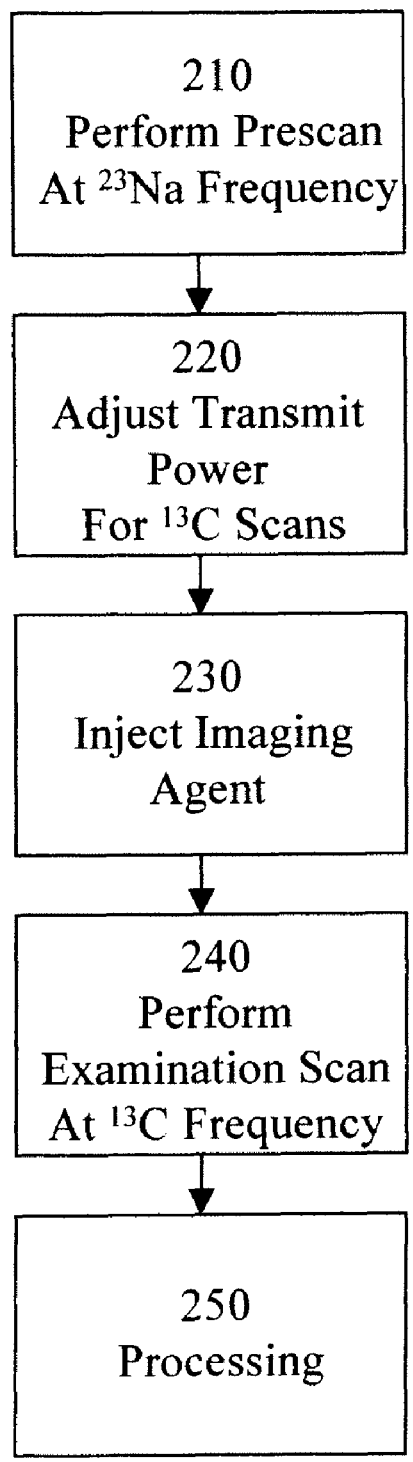
FIG. 2 is a block diagram showing an embodiment of a method for imaging using labeled contrast agents.

Referring now to FIG. 2, an embodiment of a method 200 for imaging using a labeled contrast agent is provided. As used herein, the term "labeled contrast agent" shall refer to any hyperpolarized, labeled, labeled and hyperpolarized or injected imaging agent, such as but not limited to $^{13}$C labeled pyruvate. Labeled contrast agents have been shown to improve imaging and signal, and molecules can be labeled in a number of different ways. For illustration purposes, the agent shall be $^{13}$C labeled (hyperpolarized) compounds, but it is to be appreciated that other injected agents may be employed, and whose imaging process may benefit from the methods described herein. The method comprises the following steps: performing a prescan calibration 210, adjusting 220 the transmit power according to the information obtained during the prescan, injecting or administering 230 the subject with the labeled contrast agent, performing the acquisition or examination scan 240 and signal processing 250. It is to be appreciated that prior to operation of the scanner, general scanner and coil calibration is performed at the manufacturing stage, and is not shown in FIG. 2.

In the prescan calibration step 210, the prescan is performed at a frequency selected to be substantially similar to an expected frequency of the labeled contrast agent. For example, in an exemplary embodiment of the present invention, it can be determined that the resonating frequency for $^{13}$C and $^{23}$Na are very close to one another. By employing this phenomenon, the methods and system may allow precise flip angle calibration for $^{13}$C scans in the presence of injected, $^{13}$C labeled (hyperpolarized) compounds. In an embodiment, the prescan may be based on a flip angle calibration at the $^{23}$Na frequency, prior to agent injection. $^{23}$Na is present in most tissues at relatively large concentrations (10-140 mM), allowing one to calibrate the transmit power for the desired flip angle at its resonant frequency. $^{13}$C and $^{23}$Na nuclei resonate very close to each other (16.06 MHz vs 16.89 MHz at 1.5 T), and the process of imaging at both frequencies can make use of the same transmit and receive chain (amplifier, transmit/receive (T/R) switch). As will be described in more detail with reference to FIG. 3, it can be appreciated that only minor modifications to a conventional birdcage coil are needed for a coil to resonate and acquire signals/images at both frequencies. The theoretical relationship between the power needed for the same flip angle at the two frequencies is theoretically calculated and experimentally verified, yielding a calibration curve for the coil. This calibration curve and flip angle measurements at the $^{23}$Na frequency were then used to predict the transmit power for the same flip angle needed at the $^{13}$C frequency for 4 rats. The theoretical predictions are compared to the experimentally measured $^{13}$C power levels for achieving the desired flip angles in rats. Excellent agreement is noted between the theoretical predictions and experimental measurements.

The condition to have equal flip angles on two coil channels resonating at two different frequencies can be written as $$\gamma_{13_C} B_1{}^{13_C} t_{13_C} = \gamma_{23_{Na}} B_1{}^{23_{Na}} t_{23_{Na}} \quad (1)$$

Here, the symbols have their usual meaning, depicting the gyromagnetic ratio ($\gamma$), the radio-frequency field strength ($B_1$), and the duration of the excitation pulses (t) for the two nuclei. Assuming equal length excitation pulses on the two channels, Eq. 1 can be rewritten as $$B_1{}^{13_C} = c_1 B_1{}^{23_{Na}} \quad (2)$$

Here, the proportionality coefficient $c_1$ has a theoretical value of $$c_1 = \gamma_{23_{Na}} / \gamma_{13_C} = 1.05 \quad (3)$$

To calibrate the transmit power for a given flip angle, one typically adjusts the transmit gain (TG) in a prescan step. TG represents the transmit power expressed in units of 0.1 dB (1 TG unit=0.1 dB). As the power needed for a given flip angle is proportional to the square of the $B_1$ field, one can write $$P_{13_C}[mW] = P_{23_{Na}}[mW] \cdot c_1^2 \quad (4)$$

or alternatively, $$P_{13_C}[\text{TG units}] = P_{23_{Na}}[\text{TG units}] + 200 \log c_1 \quad (5)$$

Equal excitation pulse widths have been assumed on the two channels for Eqs 4 and 5.

Therefore, as shown in FIG. 2, in an embodiment of the present invention, prior to performing prescan calibration step 210, a scanner calibration and coil calibration (not shown) is performed. It should be noted that scanner and coil calibration is performed once during the manufacturing process. Such calibration (using phantoms simulating a large range of coil loadings) is performed for each coil, relating the power needed for equal flip angles at the two different frequencies (e.g. $^{13}C$ and $^{23}Na$). The intercept of the linear fit to the data can then be used to extract the exact value of the proportionality constant $c_1$, which is a coil constant and should not change with coil loading. The value of the proportionality constant $c_1$ can be slightly different than its theoretical value of 1.05 (Eq. 3), due to factors such as non-linearity of the RF amplifier, non-equal performance of the T/R switch at the two frequencies, or non-identical tuning and matching of the 2 coil channels.

For all the ensuing in vivo measurements, the desired flip angle is only calibrated in a single prescan step 210 at the $^{23}Na$ frequency, and then the transmit power is adjusted according to the coil calibration curve for the same flip angle at the $^{13}C$ frequency as shown in step 220. All the typical prescan steps (such as center frequency localization, shimming and flip angle setup) can be easily done at the $^{23}Na$ frequency. Once all these steps are performed, the center frequency can be changed and the examination scan, or $^{13}C$ scan, is then performed at step 240. Once the examination scan is performed, processing of the acquired signals is done at step 250 using well-known techniques for MRI image processing. As described above, in embodiments, the transmit power may be adjusted based on the prescan prior to the examination scan. Processing 250 may include methods adapted to show or characterize metabolic regions of interest, as well as quantify metabolic concentrations in a region of interest.

Figure 3:
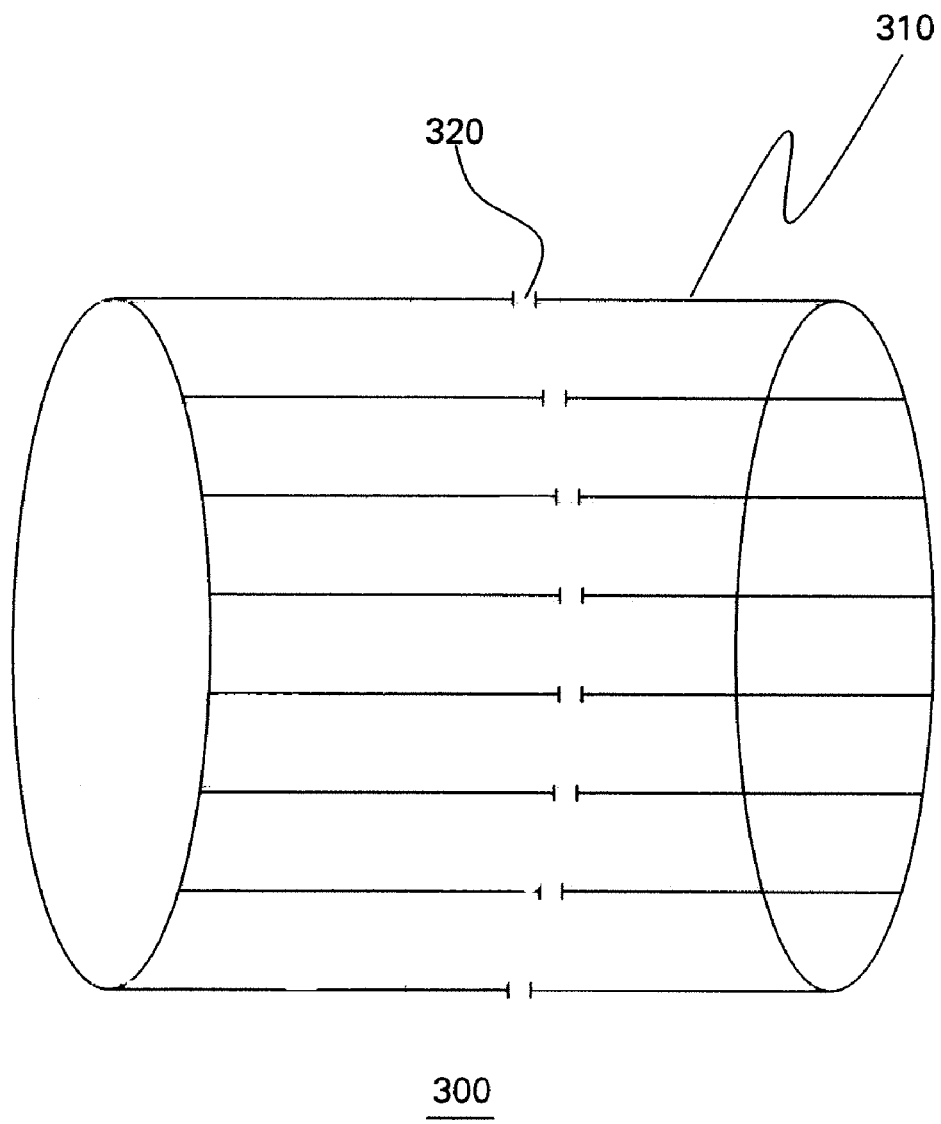
FIG. 3 is a schematic illustration of an exemplary embodiment of a radiofrequency birdcage coil to which embodiments of the present invention are applicable.

Referring to FIG. 3, there is shown an embodiment of a radiofrequency birdcage coil to which embodiments of the present invention are applicable. Two modes are normally used for imaging in a birdcage coil. Each mode gives high uniformity in the imaging region. The modes are normally tuned to the same frequency, and provide what are known as the 'I' and "Q" channels in MR imaging. In an embodiment of the present invention, a method of tuning comprises tuning different modes of a radiofrequency coil, such as a birdcage coil, to different frequencies. One mode is tuned to the Larmour frequency of the contrast agent, at the given field strength, the other to the nearby nucleus to be used for prescan calibration. In an exemplary embodiment of the birdcage coil, a 16 rung (9 cm diameter, 18 cm length), 1.5 T low-pass birdcage rat coil is provided. In this embodiment, coil 300 comprises sixteen conductors 310 and sixteen (16) capacitors 320. It is well-known that the quantity of conductors and capacitors in a birdcage coil generally correspond in number, but that additional capacitors of varying values may also be used to achieve the equivalent performance. The coil is nominally built to resonate between the two resonant frequencies of interest (16.06 MHz for $^{13}C$ and 16.89 MHz for $^{23}Na$), using 5 mm wide copper tape. Changes in the capacitor values on the rungs lying in two orthogonal planes were then made to break the symmetry of the coil and force the existence of 2 linearly polarized fields, in a manner similar to the one described in (13) for a high-pass coil. More precisely, the values of the capacitors $C_4$, $C_8$, $C_{12}$ and $C_{16}$ (as well as $C_{14}$—the balancing capacitor) were changed with respect to the other 11 equal capacitors (having the value of 220 pF). The modified capacitor values were 333 pF, 258 pF, 380 pF, 100 pF and 194 pF for $C_4$, $C_8$, $C_{12}$, $C_{14}$ and $C_{16}$, respectively, and the coil was driven on rung 12 ($^{13}C$ channel) and 16 ($^{23}Na$ channel).

The coil can be operated in two different ways. In the first approach, one can connect one channel at a time through a single T/R switch at the MRI system (not shown). The appropriate channel is manually connected when changing the scanner transmit/receive frequency. Alternatively, both channels can also be connected simultaneously through a quadrature hybrid, and switching between one mode and the other can be accomplished by simply changing the T/R frequency of the scanner. The second operation is more convenient; however, it requires using twice the amount of power (as half the power is transmitted into a non-resonant channel).

Figure 4:
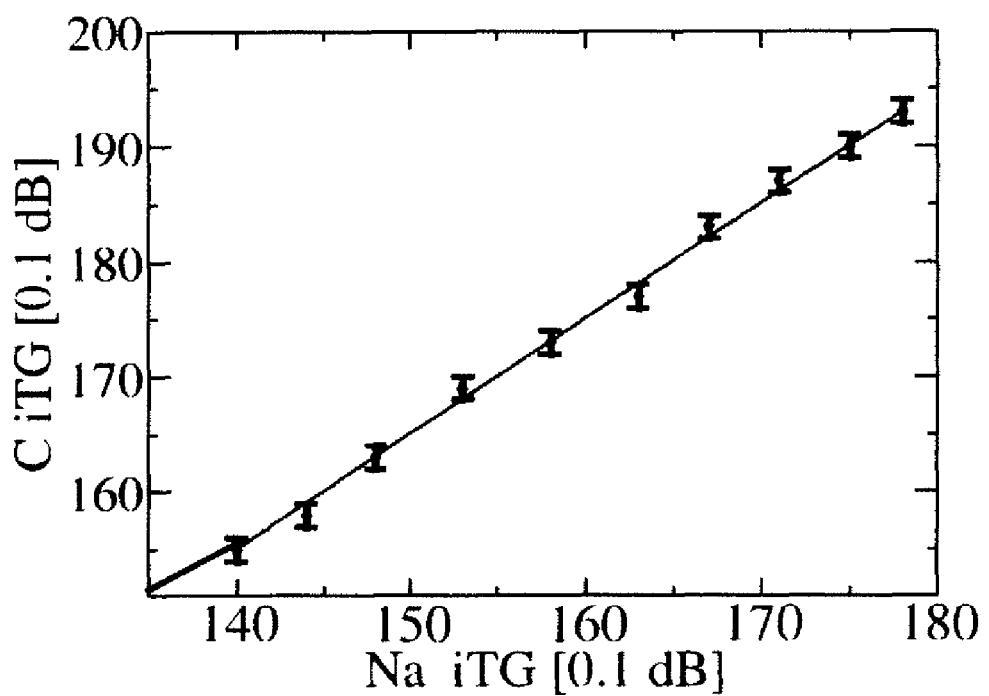
FIG. 4 is a graphic illustration showing inversion transmit gain (iTG) at the $^{13}C$ frequency (C iTG) versus the inversion transmit gain at the $^{23}Na$ frequency (Na iTG) for the dual tuned birdcage coil of FIG. 3.

To validate the theoretical framework predicting a linear dependence between the transmit power needed for a given flip angle at the $^{13}C$ and $^{23}Na$ frequencies, the inversion transmit gains at the two frequencies were measured. FIG. 4 presents a graph of the inversion transmit gains (iTG's) (TG's for the 180 degree flip angles) at the $^{13}C$ frequency versus the iTG's at the $^{23}Na$ frequency for the 10 different loading phantoms. The iTG's were measured by a scan operator in a manual prescan step, by phasing both signals in absorption mode and noting the TG's for which signals were minimized. Given the relatively high concentration of both nuclei in the phantoms, errors in measuring the iTG's were extremely low (about ±1 TG unit at the $^{13}C$ frequency, and less than this at the $^{23}Na$ frequency). As clearly noted from the graph, the relationship between the iTG's at the two different frequencies was quite linear (consistent with Eq. 5). A linear fit (performed to determine the intercept of the curve) yielded a constant of $c_1$ of 1.19 (Eq. 5) (r=0.99). The difference between the fitted value and the theoretical value of 1.05 (Eq. 3) can be easily explained by slightly difference T/R switch response at the two frequencies, slight amplifier non-linearity, different tuning matching and loading of the two coil modes. Thus, it is to be appreciated that using methods of the present invention, that precise flip angle calibration can be performed in vivo at the $^{23}Na$ frequency (where a relatively high level of signal exists in most live tissues); then the transmit gain can be increased for this particular coil by ~15 TG units (15.1=200 log(1.19)) to obtain the same flip angle on the $^{13}C$ channel.

Figure 5:
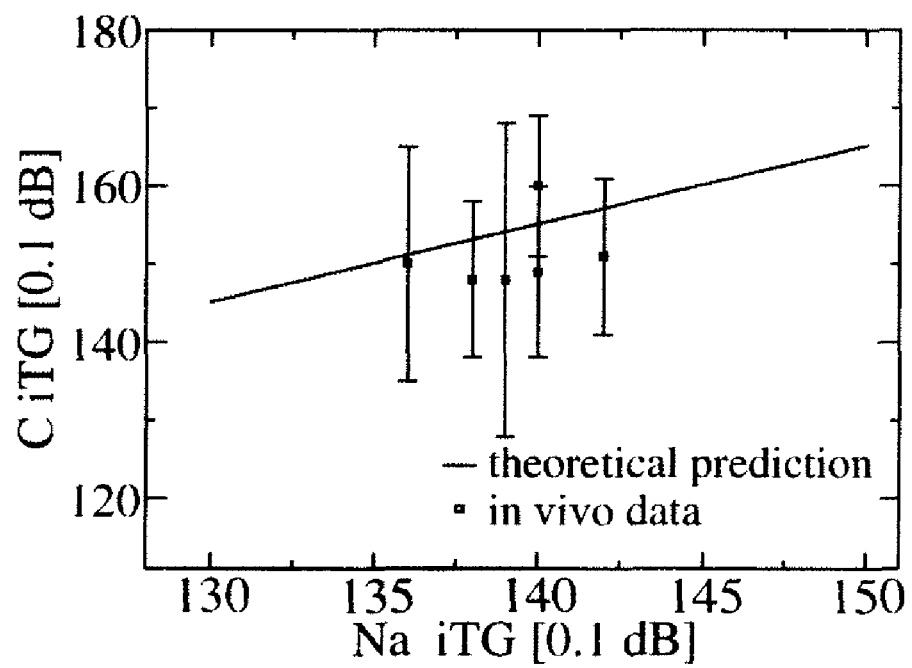
FIG. 5 is a graphic illustration showing in vivo inversion transmit gain at the $^{13}$C frequency (C iTG) versus the inversion transmit gain at the $^{23}$Na frequency (Na iTG) for experimental data acquired by imaging rats (discrete data points).

Validation of this prediction was demonstrated by scanning four rats. FIG. 5 presents six in vivo experimental data points relating the inversion transmit gain as the $^{23}Na$ frequency versus the inversion transmit gain at the $^{13}C$ frequency. The same graph also shows the calibration curve for the coil (calculated according to $TG[^{13}C]=TG[^{23}Na]+15.1$), depicted as a straight line. Notable features in FIG. 5 are:

The uncertainty in measuring the 180 degree flip angle at the $^{13}C$ frequency in vivo was large; typically, the uncertainty was on the order of ±10 TG units. However, when the head of the rat was scanned, this uncertainty can go as high as ±20 TG units. Moreover, in one of the cases, no $^{13}C$ signal could be measured from the head/neck of a rat (data point not shown). This was expected, as no significant amounts of lipids providing enough natural abundance $^{13}$C for measurements are present in the rat head.

By comparison, the error in measuring the 180 flip angle at the $^{23}$Na frequency was practically zero. In most of the cases, this uncertainty was less than 1 TG unit, confirming that most tissues provide enough $^{23}$Na signal to allow for precise calibration of transmit power for a given flip angle.

All the measured $^{13}$C transmit power values were within the predicted values from the Na measurements and the previous coil calibration. The coil calibration curve was always within the error bars for the $^{13}$C measurements, confirming the fact that accurate calibration of flip angles at the $^{13}$C frequency can be obtained from $^{23}$Na measurements (performed prior to agent injection) and the previously determined coil calibration curve.

A method has been demonstrated that allows precise flip angle calibration for $^{13}$C scans at the $^{23}$Na frequency. The major advantage of this approach is that enough natural abundance $^{23}$Na exists in tissues to allow for precise flip angle calibration at this frequency. It has been demonstrated that a linear relationship exists between the power needed to obtain a given flip angle at the $^{23}$Na and $^{13}$C frequency.

Occasions might arise, however, when this relationship can slightly depart from linearity. If the two modes of a coil (one resonating at the $^{23}$Na, and one at the $^{13}$C frequency) load differently, slight departures from linearity can be noted. These variances, however, will be observed at the time the coil calibration is performed, and the concept of doing prescan at the $^{23}$Na frequency for a $^{13}$C scan can be still used. In a further embodiment, the method may further comprises a lookup table relating transmit gains (TG), TG (carbon) with TG (sodium), will then have to be stored in the scanner memory (as opposed to just the constant $c_1$), and accessed following $^{23}$Na prescan to assess the transmit gain needed to obtain the same flip angle at the $^{13}$C frequency. It is understood that $c_1$ (or the entire calibration curve in case of nonlinearity) will be different for different coil designs, and should be measured once at the completion of the design stage (potentially as a function of coil loading, if the 2 modes load differently). It can then be used as such for any patient undergoing a $^{13}$C scan. Given the fact that both signals go through identical transmit and receive chains, slight changes in the performance of these subsystems will affect both frequencies equally, and will not require coil recalibration.

A simple implementation of a practical coil that can resonate at $^{13}$C and $^{23}$Na frequencies has also been presented. Given the fact that this low-pass coil is not being operated in quadrature drive, however, a reduction in SNR of 40% is noted at both frequencies. While this might not be a problem for the $^{23}$Na prescan, is causes undesired signal loss at the $^{13}$C frequency. Alternatively, better coils can be designed to allow for this calibration. For example, a switch-tuned, low-pass coil can be designed to operate in quadrature mode at both the $^{23}$Na and $^{13}$C frequencies. The slight change in capacitor values needed when moving from one frequency to the other can be accomplished using varactor diodes, in a manner similar to the one described in (14) for $^1$H/$^{19}$F sequential scanning. Similarly, PIN diodes can be used to add a small capacitance need to change the resonant frequency from $^{13}$C to $^{23}$Na.

As a consequence, in $^{13}$C scans involving the injection of labeled/hyperpolarized agents, anatomical localization of the region of interest can be performed using the $^1$H body coil, then a single, switch tuned coil can be used in the $^{23}$Na mode for prescan, and in the $^{13}$C mode for scan. The additional burden of using a switch-tuned ($^{13}$C/$^{23}$Na) coil is minimal, and results in net advantages, such as very precise flip angle calibration. Such calibration is not only important for certain pulse sequences to yield high SNR, artifact-free images, but it is crucial in case signal quantification is desired.

Alternatively, in another embodiment, the method for imaging may comprise to calibrating the flip angle at a different frequency than the one of $^{13}$C nuclei (or $^{23}$Na) nuclei. Given the need for anatomical localization of the regions of interest in $^{13}$C scans, and the not uncommon use of dual tuned coils ($^1$H/$^{13}$C) for scans involving the injection of a $^{13}$C labeled (hyperpolarized) compound, flip angle calibration at the $^1$H frequency would appear as a natural choice, and has been previously suggested for such purpose. In most clinical implementations of MRI scanners, however, $^1$H and $^{13}$C signals go through completely different transmit and receive chains (different RF amplifiers, as well as different T/R switches). One can potentially initially calibrate the flip angle at the proton frequency, and then predict the required transmit power at the $^{13}$C frequency. In the case that a slight change in amplifier or T/R switch performance occurs at one of the frequencies, however, consistent errors will show up in the $^{13}$C flip angle calibration. Periodic system calibrations (similar to the ones described above) would need to be performed to insure consistency of results.

A method has been developed that allows precise in vivo flip angle calibration for $^{13}$C scans in the absence of any significant $^{13}$C natural abundance signal. This method relies on the use of a dual or switch-tuned $^{13}$C/$^{23}$Na coil, and on flip angle calibration at the $^{23}$Na frequency. The NMR visibility of this nucleus allows for precise flip angle calibration in almost any organ of interest in vivo; we have demonstrated that it is straightforward to determine the power needed for a given flip angle at the $^{13}$C frequency, once the power needed at the $^{23}$Na frequency has been measured. A particular implementation of a two-channel coil, one operating at the $^{23}$Na frequency, and one at the $^{13}$C frequency (a low-pass birdcage coil forced to operate in two linear modes) was also demonstrated.

In a further embodiment, a system for imaging using a magnetic resonance imaging (MRI) scanner is provided. The system comprises a radiofrequency coil tunable at frequencies corresponding to resonating frequencies of a selected labeled contrast agent, such as $^{13C}$ labeled substance, and $^{23}$Na; and, wherein the MRI scanner is configured to perform a prescan at a $^{23}$Na frequency to calibrate the MRI scanner; and, wherein the MRI scanner is further configured to perform an examination scan at the labeled contrast agent frequency substantially immediately after administering a labeled contrast agent to a subject. In a further embodiment, the labeled contrast agent comprises an imaging agent containing $^{13}$C. As described above, the examination scan is performed to characterize a metabolic region of interest, to quantify metabolic concentrations in a region of interest or to measure flow or perfusion in a region of interest.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A method for imaging using labeled contrast agents and a magnetic resonance imaging (MRI) scanner comprising:
performing a prescan on a subject at a resonance frequency selected to be substantially similar to a resonance fre- quency of a labeled contrast agent, prior to administration of the labeled contrast agent to the subject;

performing an examination scan at the resonance frequency of the labeled contrast agent substantially immediately after administering the labeled contrast agent to the subject; and obtaining an image of the subject in order to characterize a metabolic region of interest.

2. The method of claim 1 further comprising adjusting the transmit power of the MRI scanner based on the prescan prior to performing the examination scan.

3. The method of claim 1 wherein the labeled contrast agent comprises one of a labeled, hyperpolarized, or labeled and hyperpolarized imaging agent suitable for injection.

4. The method of claim 3 wherein the labeled contrast agent comprises $^{13}C$.

5. The method of claim 1 wherein the frequency of the prescan is selected to be at a resonating frequency for $^{23}Na$.

6. The method of claim 2 wherein the transmit power is adjusted by employing a radiofrequency coil tuned at the respective frequencies of the prescan and examination scans.

7. The method of claim 3 wherein the examination scan is performed in order to quantify metabolic concentrations in a region of interest.

8. The method of claim 1 wherein the prescan comprises center frequency localization, shimming, flip angle setup and combinations thereof.

9. The method of claim 1 wherein the MRI scanner comprises a radiofrequency (RF) coil adapted to operate at two frequencies of interest, a first frequency being a prescan frequency and a second frequency being an examination frequency, wherein the coil is adapted to be either dual-tuned or switch-tuned.

10. A method for imaging with a magnetic resonance imaging (MRI) scanner comprising:

performing a prescan on a subject at a resonance frequency different than but substantially similar to a resonance frequency of a labeled contrast agent in order to calibrate the MRI scanner for a given subject, prior to administration of the labeled contrast agent to the subject;

performing an examination scan substantially immediately after administering the labeled contrast agent to the subject, wherein the examination scan is performed at a resonance frequency corresponding to the labeled contrast agent; and obtaining an image of the subject in order to characterize a metabolic region of interest.

11. The method of claim 10 further comprising adjusting the transmit power of the MRI scanner based on the prescan prior to performing the examination scan.

12. The method of claim 10 wherein the labeled contrast agent comprises one of a labeled, hyperpolarized, or labeled and hyperpolarized imaging agent suitable for injection.

13. The method of claim 12 wherein the labeled contrast agent comprises $^{13}C$.

14. The method of claim 11 wherein the transmit power is adjusted by employing a radiofrequency coil tuned at the respective frequencies of the prescan and examination scans.

15. The method of claim 10 wherein the examination scan is performed to do one of: characterizing a metabolic region of interest, quantifying metabolic concentrations in a region of interest, or measuring perfusion or flow in a region of interest.

16. The method of claim 13 wherein the prescan further comprises employing a lookup table of values relating transmit gains for a given flip angle for a nucleus used in the prescan and a nucleus used in the examination scan.

17. A system configured for imaging using a magnetic resonance imaging (MRI) scanner, the system comprising:

a radiofrequency coil tunable at frequencies corresponding to resonating frequencies of a selected labeled contrast agent and a prescan resonance frequency;

wherein the MRI scanner is configured to perform a prescan at a prescan resonance frequency in order to calibrate the MRI scanner, prior to administration of the labeled contrast agent to a subject; and, wherein the MRI scanner is further configured to perform an examination scan at the labeled contrast agent resonance frequency substantially immediately after administering a labeled contrast agent to the subject; and wherein the MRI scanner is configured to obtain an image of the subject from the examination scan characterizing a metabolic region of interest.

18. The system of claim 17 wherein the labeled contrast agent comprises one of a labeled, hyperpolarized, or labeled and hyperpolarized imaging agent that is suitable for injection.

19. The system of claim 18 wherein the labeled contrast agent comprises $^{13}C$.

20. The system of claim 17 wherein the examination scan is performed in order to do one of: quantifying metabolic concentrations in a region of interest, or measuring perfusion or flow in a region of interest.

* * * * *